(12) United States Patent
Murashima et al.

(10) Patent No.: US 7,138,263 B2
(45) Date of Patent: Nov. 21, 2006

(54) ENDOGLUCANASE ENZYME NCE5 AND CELLULASE PREPARATIONS CONTAINING THE SAME

(75) Inventors: Koichiro Murashima, Saitama (JP); Naomi Sumida, Kanagawa (JP); Akitaka Nakane, Saitama (JP); Koji Yanai, Kanagawa (JP); Tomoko Nishimura, Saitama (JP); Jinichiro Koga, Saitama (JP); Takeshi Murakami, Kanagawa (JP); Toshiaki Kono, Saitama (JP)

(73) Assignee: Meiji Seika Kabushiki Kaisha, Tokyo (JP)

( * ) Notice: Subject to any disclaimer, the term of this patent is extended or adjusted under 35 U.S.C. 154(b) by 363 days.

(21) Appl. No.: 10/276,779

(22) PCT Filed: May 22, 2001

(86) PCT No.: PCT/JP01/04272

§ 371 (c)(1),
(2), (4) Date: Nov. 19, 2002

(87) PCT Pub. No.: WO01/90375

PCT Pub. Date: Nov. 29, 2001

(65) Prior Publication Data

US 2005/0143275 A1    Jun. 30, 2005

(30) Foreign Application Priority Data

May 22, 2000   (JP) .............................. 2000-150463

(51) Int. Cl.
*C12N 9/42*      (2006.01)
*C12N 15/00*    (2006.01)
*D21B 1/08*     (2006.01)
*C11D 3/00*     (2006.01)
*C07H 21/04*   (2006.01)

(52) U.S. Cl. .............................. 435/209; 162/1; 162/4; 435/183; 435/201; 435/209; 435/252.3; 435/320.1; 510/276; 510/299; 510/300; 536/23.2

(58) Field of Classification Search ................ 435/183, 435/201, 209, 252.3, 320.1; 536/23.2; 510/276, 510/299, 300; 162/1, 4
See application file for complete search history.

(56) References Cited

U.S. PATENT DOCUMENTS

| 5,792,641 | A | 8/1998 | Schuelein et al. |
| 6,001,639 | A | 12/1999 | Schulein et al. |
| 2004/0043400 | A1 | 3/2004 | Nakane et al. |

FOREIGN PATENT DOCUMENTS

| WO | 9629397 | | 9/1996 |
| WO | WO9629397 | * | 9/1996 |
| WO | 0020555 | | 4/2000 |

OTHER PUBLICATIONS

Accession AAW04925. May 20, 1997.*
Accession AAW04925 (Schuelein et al.). May 20, 1997.*
Takashima et al., "Comparison of gene structures and enzymatic properties between two endoglucanases from *Humicola griesa*," J. Biotechnology, 67 (1999) 85-97, Elksevier Science Publishers, Amsterdam NL.
Bhat, M. K., "Cellulases and related enzyme in biotechnology," Biotechnology Advances, 18 (1999) 355-383, Elksevier Publishers, Barking GB.

* cited by examiner

*Primary Examiner*—Tekchand Saidha
*Assistant Examiner*—Christian L. Fronda
(74) *Attorney, Agent, or Firm*—Posz Law Group, PLC; R. Eugene Varndell, Jr.

(57) ABSTRACT

There is provided an endoglucanase enzyme, which is useful for reducing fuzz of regenerated cellulose-containing fabrics, improving the touch and appearance, color clarification, localized variation in color, reducing stiffness and using it as components of a detergent, as well as deinking waste paper and improving freeness of paper pulp. A cDNA coding for the endoglucanase enzyme NCE5 was cloned and its DNA sequence and amino acid sequence derived from it were determined.

29 Claims, 2 Drawing Sheets

SEQUENCE LISTING

<160> NUMBER OF SEQ ID NOS: 12

<210> SEQ ID NO 1
<211> LENGTH: 223
<212> TYPE: PRT
<213> ORGANISM: Humicola insolens

<400> SEQUENCE: 1

```
Met Gln Leu Pro Leu Thr Thr Leu Leu Thr Leu Leu Pro Ala Leu Ala
 1               5                  10                  15

Ala Ala Gln Ser Gly Ser Gly Arg Thr Thr Arg Tyr Trp Asp Cys Cys
            20                  25                  30

Lys Pro Ser Cys Ala Trp Pro Gly Lys Gly Pro Ala Pro Val Arg Thr
        35                  40                  45

Cys Asp Arg Trp Asp Asn Pro Leu Phe Asp Gly Gly Asn Thr Arg Ser
    50                  55                  60

Gly Cys Asp Ala Gly Gly Gly Ala Tyr Met Cys Ser Asp Gln Ser Pro
65                  70                  75                  80

Trp Ala Val Ser Asp Asp Leu Ala Tyr Gly Trp Ala Ala Val Asn Ile
                85                  90                  95

Ala Gly Ser Asn Glu Arg Gln Trp Cys Cys Ala Cys Tyr Glu Leu Thr
            100                 105                 110

Phe Thr Ser Gly Pro Val Ala Gly Lys Arg Met Ile Val Gln Ala Ser
        115                 120                 125

Asn Thr Gly Gly Asp Leu Gly Asn Asn His Phe Asp Ile Ala Met Pro
    130                 135                 140

Gly Gly Gly Val Gly Ile Phe Asn Ala Cys Thr Asp Gln Tyr Gly Ala
145                 150                 155                 160

Pro Pro Asn Gly Trp Gly Gln Arg Tyr Gly Gly Ile Ser Gln Arg His
                165                 170                 175

Glu Cys Asp Ala Phe Pro Glu Lys Leu Lys Pro Gly Cys Tyr Trp Arg
            180                 185                 190
```

```
            Phe Asp Trp Phe Leu Asn Ala Asp Asn Pro Ser Val Asn Trp Arg Gln
                195                 200                 205

Val Ser Cys Pro Ala Glu Ile Val Ala Lys Ser Gly Cys Ser Arg
                210                 215                 220
```

```
<210> SEQ ID NO 2
<211> LENGTH: 672
<212> TYPE: DNA
<213> ORGANISM: Humicola insolens

<400> SEQUENCE: 2
atgcagctcc ccctgaccac gctcctcacc ctcctcccccg ccctcgcggc ggcccagtcc      60
ggcagcggcc gcaccacgcg ctactgggac tgctgcaagc cgtcgtgcgc gtggcccggc     120
aagggcccgg cgcccgtgcg gacgtgcgac cggtgggaca cccgctgttc gacggcggc      180 aacacgcgca gcgggtgcga cgcgggcggc ggcgcctaca tgtgctcgga ccagagcccg     240
tgggcggtca gcgacgacct ggcgtacggc tgggcggccg tcaacattgc cggctccaac     300
gagaggcagt ggtgctgcgc ctgctacgag ctgaccttca ccagcgggcc ggtggcgggc     360
aagaggatga ttgtgcaggc gagcaacacg ggaggcgatt tggggaacaa ccactttgat     420
attgctatgc ccggcggtgg cgtcggtatc ttcaacgcct gcaccgacca gtacggcgcg     480
ccccccaacg gctgggccca cgctacggc ggcatcagcc aacgccacga gtgcgacgcc      540
ttccccgaga gctcaagcc cggctgctac tggcgctttg actggttcct caacgccgac     600
aacccgagcg tcaactggcg gcaggtcagc tgcccggccg agattgtggc caagagcggc     660
tgctcgcgtt aa                                                         672
```

```
<210> SEQ ID NO 3
<211> LENGTH: 20
<212> TYPE: PRT
<213> ORGANISM: Humicola insolens

<400> SEQUENCE: 3

Ser Gly Ser Gly Arg Thr Thr Arg Tyr Trp Asp Cys Cys Lys Pro Ser
            1               5                   10                  15

Cys Ala Trp Pro
                    20
```

```
<210> SEQ ID NO 4
<211> LENGTH: 8
<212> TYPE: PRT
<213> ORGANISM: Humicola insolens

<400> SEQUENCE: 4

Leu Lys Pro Gly Cys Tyr Trp Arg
            1               5
```

```
<210> SEQ ID NO 5
<211> LENGTH: 6
<212> TYPE: PRT
<213> ORGANISM: Humicola insolens

<400> SEQUENCE: 5

Tyr Trp Asp Cys Cys Lys
            1               5
```

```
<210> SEQ ID NO 6
<211> LENGTH: 12
<212> TYPE: PRT
```

-continued

<213> ORGANISM: Humicola insolens

<400> SEQUENCE: 6

Trp Asp Asn Pro Leu Phe Asp Gly Gly Asn Thr Arg
1               5                   10

<210> SEQ ID NO 7
<211> LENGTH: 12
<212> TYPE: PRT
<213> ORGANISM: Humicola insolens

<400> SEQUENCE: 7

Gln Trp Cys Cys Ala Cys Tyr Glu Leu Thr Phe Thr
1               5                   10

<210> SEQ ID NO 8
<211> LENGTH: 15
<212> TYPE: PRT
<213> ORGANISM: Humicola insolens

<400> SEQUENCE: 8

Phe Asp Trp Phe Leu Asn Ala Asp Asn Pro Ser Val Asn Trp Arg
1               5                   10                  15

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 9
taytgggayt gytgyaarcc                                               20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence:
      Synthetic DNA
<220> FEATURE:
<221> NAME/KEY: misc_feature
<222> LOCATION: 3...3
<223> OTHER INFORMATION: n is a, g, c, or t
<220> FEATURE:
<221> NAME/KEY: misc_feature
<222> LOCATION: 9...9
<223> OTHER INFORMATION: n is a, g, c, or t

<400> SEQUENCE: 10
tcngcrttna rraaccartc                                               20

<210> SEQ ID NO 11
<211> LENGTH: 38
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 11
ggggatcctg ggacaagatg cagctccccc tgaccacg                           38

<210> SEQ ID NO 12
<211> LENGTH: 38

```
<212> TYPE: DNA
<213> ORGANISM: Artificial Sequence
<220> FEATURE:
<223> OTHER INFORMATION: Description of Artificial Sequence:
      Synthetic DNA

<400> SEQUENCE: 12
ggggatcctg catttaacgc gagcagccgc tcttggcc                              38
```

ENDOGLUCANASE ENZYME NCE5 AND CELLULASE PREPARATIONS CONTAINING THE SAME

CROSS REFERENCE TO RELATED APPLICATIONS

This application is a U.S. national phase application of International Application No. PCT/JP01/04272, filed May 22, 2001, which claims priority from Japanese patent application No 2000-150463, filed May 22, 2000.

TECHNICAL FIELD

This invention relates to an endoglucanase, a cellulase preparation which contains the endoglucanase and a method for the treatment of a cellulose-containing fabric using the cellulase preparation.

TECHNICAL BACKGROUND

In order to add desired characteristics to a cellulose-containing fabric, the cellulose-containing fabric is treated with cellulase. For example, treatment with cellulase is carried out in the field of textile industry for the purpose of improving the touch and appearance of a cellulose-containing fabric or adding a "stone wash" appearance which provides a localized variation in color of colored cellulose-containing fabrics (European Patent 307,564).

Currently, cellulase preparations derived from wood rotting fungi *Trichoderma* and *Humicola* are used for the purpose of adding stone wash appearance to dyed-denim cellulose-containing fabric and improving the touch of the same. These cellulase preparations are mixtures of plural cellulase components. Their practical use has been hindered by a difficulty resulting from the necessity to use a large amount of the cellulase preparation for exerting desired effect on the cellulose-containing fabric.

Such a disadvantage of the cellulase preparation is being improved by using a preparation which contains a large amount of endoglucanases. For example, cellulase preparations having enriched endoglucanase activity are published by international publications WO 89/09259, WO 91/17243, WO 98/03640 and WO 94/21801. Particularly, WO 91/17243 discloses that a purified 43 kD endoglucanase component (EGV) derived from *Humicola* has a jeans abrasive activity which is about 100 times higher than that of a conventionally known cellulase preparation as a mixture of a plurality of cellulase components. Also, WO 98/03640 discloses that an endoglucanase component NCE4 derived from *Humicola* has a 25 times higher jeans abrasive activity and 100 times higher lyocell fuzz removing activity in comparison with a conventionally known cellulase preparation as a mixture of a plurality of cellulase components.

Such a treatment with cellulase has been carried out with the aim of adding stone wash appearance to a dyed-denim cellulose-containing fabric and improving the touch of the same, but in that case, it causes problems such as redeposition or redyeing of a portion of indigo dye on clothing, namely back-staining, during the treatment process.

There is a method as an attempt to lower degree of the back-staining, in which indigo dye is dispersed in a cellulase treating solution by adding a reagent such as a surfactant. However, this method has problems in that it requires a cost for the adding chemical product and increases environmental load of waste water.

Accordingly, concern has been directed toward the provision of a cellulase having high activity but low degree of back-staining, to be used in the treatment of dyed-denim cellulose-containing fabric.

DISCLOSURE OF THE INVENTION

This time, the present inventors have isolated a novel endoglucanase enzyme NCE5 having high activity to disintegrate cellulose fabrics and its gene from a mold *Humicola insolens* and showed that this enzyme has a structure having no precedent for an enzyme which is derived from *Humicola* and hydrolyzes cellulose fabrics, namely it has a small molecular weight of about 25 kDa and a cellulose binding domain (CBD) is not present in the structure.

It was shown also that, in the treatment of a dyed-denim cellulose-containing fabric with a preparation obtained by expressing the enzyme NCE5 using *Humicola insolens* as the host, the enzyme shows a high activity similar to NCE4, while surprisingly showing that the degree of back-staining is low in comparison with NCE4.

Accordingly, the invention contemplates providing a cellulase having low degree of back-staining in the treatment of dyed-denim cellulose-containing fabric and its gene.

The invention also contemplates providing a cellulase preparation having excellent characteristics.

In addition, the invention contemplates providing a method for the efficient and inexpensive treatment of cellulose-containing fabric, which uses this enzyme.

This application includes part or all of the contents as disclosed in the specification and/or drawings of Japanese Patent Application No. 2000-150463, which is priority documents of the present application.

BEST EMBODIMENT OF CARRYING OUT THE INVENTION

The following describes the invention in detail.

Cellulase

The endoglucanase enzyme NCE5 provided by the invention has an advantageous property in that the degree of back-staining is low in comparison with NCE4 in the treatment of a dyed-denim cellulose-containing fabric. Thus, according to the enzyme of the invention, the amount of a chemical product to be added such as a surfactant can be reduced in the treatment of a dyed-denim cellulose-containing fabric and, as a result, reduction of cost can be realized and reduction of load on environment can be achieved.

This enzyme is a novel protein which shows homology with the *H. grisea* egl4 sequence reported by S. Takashima et al. (S. Takashima et al., *Journal of Biotechnology*, 67, 85–97 (1999)). This enzyme has characteristics in that it has a small molecular weight of about 25 kDa and a cellulose binding domain (CBD) does not exist in its structure. In a state of nature, all of the enzymes which have been isolated from a mold *Humicola* having a high activity to disintegrate cellulose fabrics contained the cellulose binding domain (CBD) (e.g., a purified 43 kD endoglucanase component (EGV) derived from *Humicola* has been disclosed in WO 91/17243, and a *Humicola*-derived endoglucanase component (NCE4) in WO 98/03640). However, a *Humicola*-derived enzyme containing no CBD but having a high activity to disintegrate cellulose has not been known in the natural world.

As an endoglucanase which does not contain CBD among enzymes derived from a mold other than *Humicola*, JP-W-

8-507695 (the term "JP-W" as used herein means an "unexamined published Japanese international patent application") discloses that EGIII isolated from *Trichoderma longibrachiatum* has an optimum pH as its CMCase activity (Remazol Brilliant Blue carboxymethylcellulose assay) of from 5.5 to 6.0 and has a high activity even at neutral to alkaline range in comparison with the conventionally known *Trichoderma*-derived cellulase. On the other hand, CMCase activity of the enzyme of the invention has an optimum pH of from 5.0 to 9.0 and shows a high activity at more alkaline range in comparison with EGIII.

This enzyme is a protein which has a part or from a 19th to 223rd position sequence of the sequence described in SEQ ID NO:1. According to the invention, the term "a part of the sequence described in SEQ ID NO:1" means, for example, a length which can be used as a probe, more illustratively a partial sequence which still keeps cellulase activity, particularly endoglucanase activity.

A protein which further contains a part or entire portion of an amino acid sequence of from the 1st to 18th positions described in SEQ ID NO:1 in the N-terminal side of the above protein is also included in the invention. In this connection, since the amino acid sequence of from the 1st to 18th positions described in SEQ ID NO:1 is considered to be the signal peptide, the part of the sequence means a sequence remained in the N-terminal as a result of the generation of a difference at a position to be processed by the type of expression host, in addition to its partial sequence which keeps the signal peptide activity.

A modified protein of the above protein is also included in the invention. According to the invention, the modified protein means a protein in which a modification such as addition, insertion, elimination, deletion or substitution of at least 1, preferably from 1 to several, of amino acids is generated in the amino acid sequence of the above protein, but still keeping the cellulase activities, particularly endoglucanase activity.

The enzyme of the invention can be obtained from molds, illustratively a microorganism belonging to the genus *Humicola* (e.g., *H. insolens*).

According to the invention, a nucleotide sequence which encodes the amino acid sequence described in SEQ ID NO:1 or a modified protein thereof is provided. Once the amino acid sequence of a protein is given, a DNA sequence coding for the same is easily determined, so that various nucleotide sequences which encode the amino acid sequence described in SEQ ID NO:1 or a modified protein thereof can be selected.

The nucleotide sequence of the invention may be either a natural origin or a product of total synthesis, or it may be a product synthesized by making use of a part of the natural origin. Typical examples of the method for obtaining the nucleotide sequence of the invention include a method in which it is screened from a cDNA library of *Humicola insolens* by a technique conventionally used in the field of genetic engineering, for example using an appropriate DNA probe prepared based on the information of a partial amino acid sequence.

A typical sequence which encodes the amino acid sequence of endoglucanase NCE5 of the invention has a part or entire portion of the nucleotide sequence described in SEQ ID NO:2. The nucleotide sequence described in SEQ ID NO:2 has an open reading frame which starts with the 1st to 3rd position ATG and completes with the 670th to 672nd TAA. Also, the 55th to 57th nucleotide sequence corresponds to the N-terminal amino acid of the mature protein composed of 205 residues.

Endoglucanase Activity

Endoglucanase activity means "CMCase activity", which is an activity for hydrolyzing generally carboxymethylcellulose. One unit of "CMCase activity" is defined as an amount of the enzyme forming reducing sugars corresponding to 1 μmol of glucose, which is determined by a method which comprises incubating a protein to be tested and CMC solution for a fixed time and then determining a reducing sugars liberated. In addition, "CMCase activity" is determined also by a method using as a standard a change in viscosity of the CMC solution to which a protein to be tested is added.

In the present invention, according to the method of Neena Din et al. (Neena Din et al., *Biotechnology*, 9 (1991), 1096–1099), endoglucanase activity is determined using absorbant cotton fibril-releasing activity as a standard. That is, the amount of fibril released from absorbent cotton when a protein to be tested, stainless beads and absorbent cotton are added to 50 mM phosphate buffer solution (pH7), reacted in Launder Meter (L-12, Daiei Kagaku Seiki MFG., Japan) at 55° C. for 120 minutes and then an amount of fibril released from absorbent cotton is measured at an absorbance of 600 nm.

Expression Vector and Transformed Microorganism

The invention also provides an expression vector which can replicate the nucleotide sequence coding for the amino acid sequence described in SEQ ID NO:1 or a modified protein thereof in a host microorganism (The following merely describes "the DNA sequence of the invention".) and contains a DNA sequence in such a state that the protein encoded thereby can be expressed. The expression vector of the invention can be constructed based on a self-replication vector such as a plasmid which exists in an independent form outside the chromosome and whose replication does not depend on the replication of chromosome. Also, the expression vector of the invention may be a vector which is integrated into a genome of a host microorganism when introduced into the host microorganism and replicated together with the chromosome into which it is integrated. Regarding the procedure and method for the construction of the vector of the invention, those which are generally used in the field of genetic engineering can be used.

In order to effect expression of a protein having a desired activity by practically introducing the expression vector of the invention into a host microorganism, it is desirable that the vector contains not only the DNA sequence of the invention but also other elements such as a DNA sequence which controls the expression and a gene marker for selecting a microoganism. As the DNA sequence which controls the expression, a promoter, a terminator and a DNA sequence coding for a signal peptide are included therein. The promoter is not particularly limited, with the proviso that it can show its transcription activity in a host microorganism, and can be obtained as a DNA sequence which controls the expression of a gene that encodes a protein either identical to or different from that of the host microorganism. Also, the signal peptide is not particularly limited, with the proviso that it can contribute to the secretion of protein in a host microorganism, and can be obtained from a DNA sequence derived from a gene which encodes a protein either identical to or different from that of the host microorganism. In addition, the gene marker according to the invention may be optionally selected in response to the selection method of transformants, for example, a gene coding for a drug resistance or a gene which complements auxotrophy can be used.

In addition, according to the invention, a microorganism transformed with this expression vector is provided. This host-vector system is not particularly limited, for example, a system in which *Escherichia coli*, an actinomycetes, a yeast or a mold is used and a fusion protein expression system with other protein using the same can be used.

Also, transformation of a microorganism with this expression vector can be carried out in accordance with the techniques generally used in this field.

In addition, by culturing the resulting transformant using an appropriate medium, the protein of the invention can be obtained by isolating it from the culture mixture. Thus, according to another embodiment of the invention, a method for the production of the novel protein of the invention is provided. Culturing of the transformant and its conditions may be basically the same as those of the used microorganism. After culturing of the transformant, the protein of interest can be recovered by a method generally used in this field.

Also, according to a preferred embodiment of the invention, a yeast cell capable of expressing endoglucanase enzyme encoded by the DNA sequence of the invention are provided. Examples of the yeast cell of the invention include microorganisms belonging to the genus *Saccharomyces*, the genus *Hansenula* or the genus *Pichia*, for example *Saccharomyces cerevisiae*.

The host mold according to the invention may be a mold which belongs to the genus *Humicola*, the genus *Aspergillus*, the genus *Trichoderma*, the genus *Fusarium* or the genus *Acremonium*. Its preferred examples include *Humicola insolens, Aspergillus niger* or *Aspergillus oryzae, Trichoderma viride, Fusarium oxysporum* and *Acremonium cellulolyticus*.

Deposition of Microorganism

*Humicola insolens* MN200-1 has been deposited in the National Institute of Advanced Industrial Science and Technology, an Independent Administrative Institution under the Ministry of Economy, Trade and Industry, AIST Tsukuba Central 6, Higashi 1-1-1, Tsukuba, Ibaraki, Japan under an accession number FERM BP-5977 (original deposit: FERM P-15736, original deposit date: Jul. 15, 1996). An *Escherichia coli* strain JM109 transformed with a plasmid pNCE5Bam containing the cellulase gene of the invention (cf. Example 4) has been deposited on Apr. 18, 2000, in the National Institute of Advanced Industrial Science and Technology, an Independent Administrative Institution under the Ministry of Economy, Trade and Industry, AIST Tsukuba Central 6, Higashi 1-1-1, Tsukuba, Ibaraki, Japan under an accession number FERM BP-7138.

An *Escherichia coli* strain (*Escherichia coli*/pEGD01) transformed with a plasmid pEGD01 has been deposited in the National Institute of Advanced Industrial Science and Technology, an Independent Administrative Institution under the Ministry of Economy, Trade and Industry, AIST Tsukuba Central 6, Higashi 1-1-1, Tsukuba, Ibaraki, Japan under an accession number FERM BP-5973 (original deposit: FERM P-15729, original deposit date: Jul. 12, 1996).

Use of Cellulase/Cellulase Preparation

According to still another embodiment of the invention, a cellulase preparation containing an endoglucanase enzyme, and its modified peptide of the present invention is provided. The cellulase preparation of the invention may contain other types of cellulase, such as cellobiohydrase, β-glucosidase and endoglucanase other than that of the invention, in addition to the endoglucanase enzyme and its modified peptide of the invention, and may be produced by further mixing the cellulase preparation with generally used components such as fillers (e.g., lactose, sodium chloride and sorbitol), surfactants and antiseptics. Also, the cellulase preparation of the invention can be prepared into any suitable shape such as a powder or liquid form.

The invention also provides a method for clearing color of a colored cellulose-containing fabric, which comprises a step of treating the colored cellulose-containing fabric with an endoglucanase enzyme or a cellulase preparation, and a method for providing a localized variation in color of a colored cellulose-containing fabric, namely a method for giving a stone wash appearance to the colored cellulose-containing fabric. This method comprises a step of treating the colored cellulose-containing fabric with the endoglucanase enzyme or cellulase preparation of the invention.

Such methods of the invention can be carried out by treating the cellulose-containing fabric during washing. In some cases, however, the treatment of fabric may be carried out by adding the endoglucanase enzyme or cellulase preparation of the invention to water in which the fabric is soaked or to be soaked during soaking or rinsing.

The invention further provides a method of reducing the rate at which a cellulose-containing fabric becomes fuzzy or reducing fuzzing in such a fabric; or a method of reducing the rate at which a cellulose-containing fabric becomes stiff or reducing stiffness in such a fabric. Each of these methods comprises a step of treating the cellulose-containing fabric with the endoglucanase enzyme or cellulase preparation of the invention.

Its conditions such as the contacting temperature or the amount of endoglucanase enzyme may be appropriately decided considering other various conditions. For example, in the case of a weight loss treatment of a cellulose-containing fabric to improve its touch and appearance, the fabric can be treated at a temperature of approximately from 50 to 60° C. using the endoglucanase having a protein concentration of from 1 to 100 mg/L. Also, when a localized variation in color of a colored cellulose-containing fabric is desired, it can be treated at a temperature of approximately from 50 to 60° C. using the endoglucanase having a protein concentration of from 2 to 50 mg/L.

Also, when the rate at which a cellulose-containing fabric becomes fuzzy is reduced or fuzzing in such a fabric is reduced, it can be treated at a temperature of approximately from 50 to 60° C. using the endoglucanase enzyme having a protein concentration of from 0.05 to 10 mg/L.

Also, by the use of the endoglucanase enzyme or cellulase preparation of the invention in a detergent composition, granular soil removal, color clarification, defuzzing, de-pilling and reduction of stiffness can be improved. The detergent composition defined by the invention can contain a surfactant (an anionic, nonionic, cationic, amphoteric or zwitter ionic agent or a mixture thereof).

The detergent composition of the invention can also contain other detergent components well known in this field, such as a builder, a bleaching agent, a bleaching active agent, a corrosion inhibitor, a sequestering agent, a stain dissociating polymer, a perfume, other enzyme (such as protease, lipase or amylase), an enzyme stabilizer, a formulation assisting agent, an optical brightener and a foam accelerating agent. Typical examples of the anionic surfactant include linear alkyl benzene sulfonate (LAS), alkyl sulfate (AS), alpha-olefin sulfonate (AOS), alcohol ethoxy sulfate (AES) and alkali metal salts of natural fatty acids. Examples of the nonionic surfactant include polyoxyethylene alkyl ether (AE), alkyl polyethylene glycol ether, nonylphenol polyethylene glycol ether, fatty acid esters of sucrose and glucose, and esters of polyethoxylated alkyl glucoside.

It was found that deinking can be effected by allowing the endoglucanase enzyme or cellulase preparation of the invention to react with waste paper. Thus, a process for making recycled paper from waste paper can be improved significantly by its treatment with the endoglucanase enzyme of the invention. All of the generally called waste paper can be used as the waste paper to be used in the invention, and their examples include those of newspaper, magazines and printed primary to secondary grade paper, produced by bending mechanical pulp and chemical pulp, waste of wood-free paper comprised of chemical pulp and waste of printed paper such as coating paper thereof.

Also, the term "deinking agent" as used herein means an agent generally used for deinking waste paper, and its examples include an alkaline compounds such as NaOH and $Na_2CO_3$, sodium silicate, hydrogen peroxide and phosphates, as well as anionic and nonionic surfactants, scavengers such as oleic acid and auxiliaries such as a pH stabilizer, a chelating agent and a dispersing agent.

Also, according to the invention, it is considered that treatment of paper pulp with the endoglucanase enzyme of the invention renders possible significant improvement of its freeness without causing considerable reduction of paper strength. Thus, according to the invention, there is provided a method for improving freeness of paper pulp, which comprises a step of treating paper pulp with the endoglucanase enzyme or cellulase preparation of the invention. Examples of the pulp which can be treated by the invention include waste pulp, recycled board pulp, kraft pulp, sulfite pulp and thermo-mechanical treatment and other high yield pulp.

In addition, the ability to digest glucan in animal feed can be improved by adding the endoglucanase of the invention in the feed. Thus, according to the invention, there is provided a method for improving digestion ability of animal feed, which comprises a step of treating animal feed with the endoglucanase enzyme or cellulase preparation of the invention.

EXAMPLES

Figure 1:
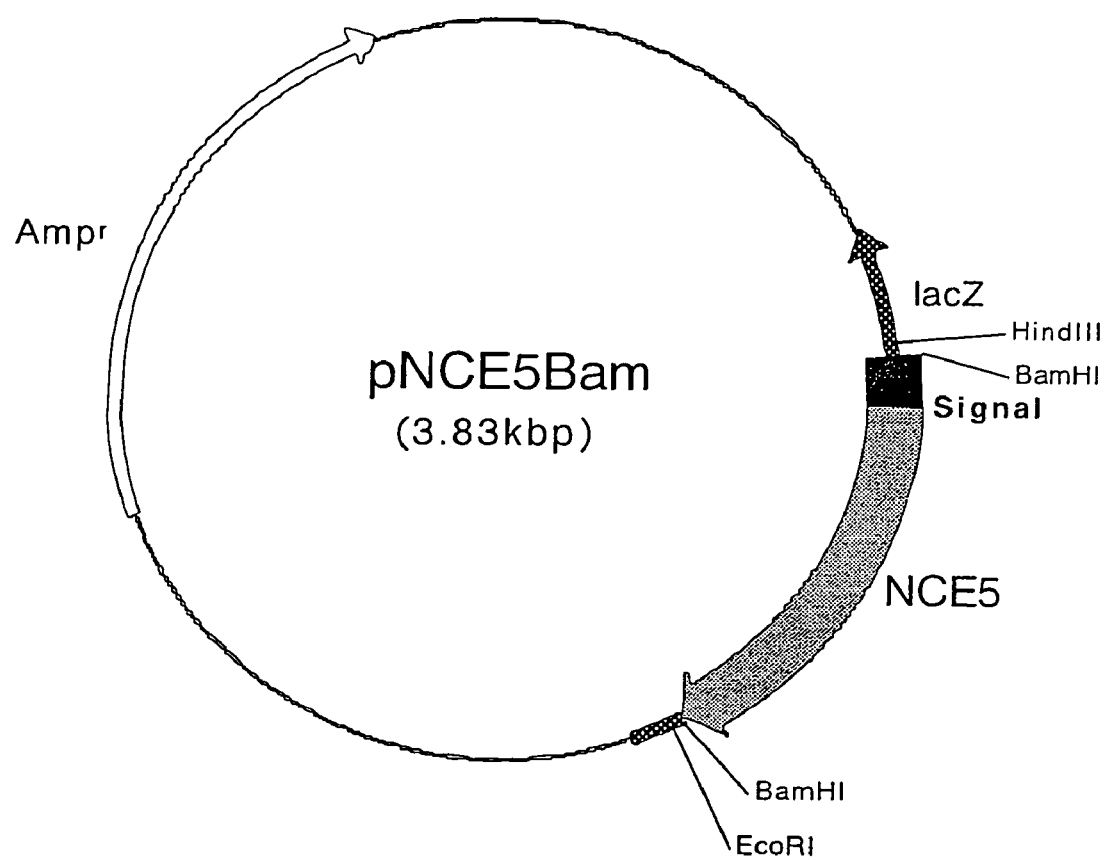
FIG. 1 represents a constitution of plasmid pNCE5Bam.

The invention is described more illustratively with reference to examples, but the invention is not limited to the following examples without overstepping its scope.

Example 1

Isolation and Purification of a Component Having Absorbent Cotton Fibril-Releasing Activity from *Humicola insolens*

*Humicola insolens* MN200-1 (FERM BP-5977) was inoculated into an (N) medium (5.0% Avicel, 2.0% yeast extract, 0.1% peptone, 0.03% calcium chloride, 0.03% magnesium chloride, pH 6.8) and cultured at 37° C. on a shaker. After 7 days of the culturing, the thus obtained culture broth was centrifuged at 7,000 rpm for 20 minutes to remove the cells, and the resulting culture filtrate was used as a crude cellulase preparation solution.

A 200 ml portion of this crude cellulase preparation solution was adjusted to a solution of 1 M in final concentration ammonium sulfate and then applied at a flow rate of 20 ml/min to a Source PHE column (gel volume 150 ml, mfd. by Amersham Pharmacia Biotech) which had been equilibrated in advance with 1 M ammonium sulfate solution. Next, this was eluted and fractionated by a linear gradient elution of from 1.0 M to 0 M ammonium sulfate concentration in 50 mM phosphate buffer (pH 7.0) at a flow rate of 20 ml/min. Among these fractions, strong cotton fibril-releasing activity was found in a part of fractions obtained when the ammonium sulfate concentration was 0.3 M. Thus, 200 ml of this fraction was collected. This step was carried out twice.

A 400 ml portion of the thus obtained active fraction was adjusted to 1.5 M ammonium sulfate concentration in 50 mM phosphate buffer (pH 7.0) and then applied at a flow rate of 20 ml/min to a Source ISO column (gel volume 125 ml, mfd. by Amersham Pharmacia Biotech) which had been equilibrated in advance with 1.5 M ammonium sulfate solution in 50 mM phosphate buffer (pH 7.0). Next, this was eluted and fractionated by a linear gradient elution of from 1.5 M ammonium sulfate concentration in 50 mM phosphate buffer (pH 7.0) to ultra-pure water at a flow rate of 20 ml/min. Among these fractions, strong absorbent cotton fibril-releasing activity was found in a part of fractions obtained when the ammonium sulfate concentration was 1.05 M. Thus, 200 ml of this fraction was collected.

Next, ammonium sulfate was added to a level of 65% saturation to 200 ml of the thus obtained active fraction, and the mixture was stirred at 4° C. for 60 minutes and then centrifuged at 15,000 rpm to recover the precipitate. This precipitate was dissolved in 20 ml of distilled water and subjected to desalting using Ultrafree/Biomax-5K (Millipore) to recover 40 ml of solution.

A 30 ml portion of the thus obtained active fraction was adjusted to 50 mM acetate buffer (pH 4.0) and then applied at a flow rate of 5 ml/min to an SP Sepharose FF column (gel volume 16 ml, mfd. by Amersham Pharmacia Biotech) which had been equilibrated in advance with 50 mM acetate buffer (pH 4.0). Next, this was eluted and fractionated by a linear gradient elution of from 50 mM acetate buffer (pH 4.0) to 1 M NaCl in 50 mM acetate buffer (pH 5.0) at a flow rate of 4 ml/min. Among these fractions, strong absorbent cotton fibril-releasing activity was found in a part of fractions obtained when the NaCl concentration was about 0.12 M. Thus, 12 ml of this fraction was collected.

Thereafter, a 6 ml portion of the thus obtained active fraction was adjusted to 50 mM acetate buffer (pH 4.0) and then applied at a flow rate of 1 ml/min to a Mono S 5/5HR column (mfd. by Amersham Pharmacia Biotech) which had been equilibrated in advance with 50 mM acetate buffer (pH 4.0). Next, this was eluted and fractionated by a linear gradient elution of from 50 mM acetate buffer (pH 4.0) to 1 M NaCl in 50 mM acetate buffer (pH 5.0) at a flow rate of 1 ml/min. Among these fractions, strong absorbent cotton fibril-releasing activity was found in a part of fractions obtained when the NaCl concentration was about 0.1 M. Accordingly, 1 to 3 ml of this fraction was collected. This fraction was isolated as NCE5. This NCE5 showed a single band of 25 kD by an SDS-PAGE. By repeating the above purification steps of NCE5 50 times, a purified sample was obtained in a large amount.

The SDS-PAGE was carried out using a system provided by Tefco. That is, an electrophoresis vessel (No. 03-101), a power source (Model 3540), a 10% gel (0 1-075) and a buffer kit for SDS-PAGE use (06-0301) were used. The electrophoresis conditions were 18 mA/10 minutes and then 20 mA/90 minutes. For the detection of protein after the electrophoresis, silver staining was carried out using 2D-Silver Staining Reagent II "Daiichi" for Electrophoresis Use (mfd. by Daiichi Pure Chemicals). As the standard marker protein, an SDS-PAGE molecular weight standard protein Low Range (161-0304) mfd. by Bio-Rad was used.

The absorbent cotton fibril-releasing activity was measured by a modified method of the method of Neena Din et al. (Neena Din et al., *Biotechnology*, 9 (1991), 1096–1099). That is, the amount of fibril released from absorbent cotton when reacted under the following conditions using a launder meter was measured at an absorbance of 600 nm.

| Testing machine | Launder Meter L-12 (Daiei Kagaku Seiki MFG., Japan) |
| --- | --- |
| Temperature | 55° C. |
| Time | 120 minutes |
| Reaction pH | pH 7 (50 mM phosphate buffer) |

To the treating solution were added appropriate amounts of stainless beads and absorbent cotton together with an endoglucanase solution.

Example 2

Partial Amino Acid Sequence of Cellulase NCE5

(1) Identification of N-Terminal Amino Acid Sequence

In order to determine N-terminal amino acid sequence of the protein purified in Example 1, the NCE5 fraction was treated with SDS-PAGE mini (mfd. by Tefco), transferred on a PVDF membrane by electroblotting, stained with Coomassie Brilliant Blue R250 (mfd. by Nakalai Tesque), decolorized, washed with water and then air-dried. When the portion where a 25 kDa protein was blotted was cut out therefrom and applied to a protein sequencer Model 492 (mfd. by PE Applied Biosystems) in an attempt to analyze the N-terminal amino acid sequence, a signal by Edman degradation was not obtained, so that it was revealed that the N-terminal amino acid was modified and protected. Accordingly, the membrane was soaked in 0.5% polyvinylpyrrolidone (molecular weight 40,000, mfd. by Sigma)/100 mM acetic acid solution at 37° C. for 30 minutes to effect blocking of protein unbinding moiety on the membrane, the modified N-terminal residue was removed by treating it with Pfu Pyroglutamate Aminopeptidase (mfd. by Takara Shuzo) at 50° C. for 5 hours, and then the sequencing was carried out again. The thus obtained sequence was as follows.

N-terminal Amino Acid Sequence of NCE5
Ser-Gly-Ser-Gly-Arg-Thr-Thr-Arg-Tyr-Trp-Asp-(Cys)-(Cys)-Lys-Pro-Ser-(Cys)-Ala-Trp-Pro (20 residues) (SEQ ID NO:3)

(2) Peptide Mapping

In order to determine internal amino acid sequence of the protein purified in Example 1, the protein was subjected to reductive alkylation and then its peptide mapping was carried out.

That is, 300 μg of the purified protein was dissolved in 500 μl of a reductive alkylation buffer (0.5 M tris, 7 M guanidine hydrochloride, 10 mM EDTA·2Na$_2$) in a tube, and then 1 mg of DTT was added thereto. The air in the tube was replaced with nitrogen, and the contents were kept at room temperature for 5 hours to carry out reduction of the protein. After the reducing reaction, 2.5 mg of monoiodoacetic acid was added thereto to carry out alkylation reaction at room temperature for 30 minutes under shading. After the reaction, the reaction mixture was dialyzed against distilled water to effect desalting and then freeze-dried, and the thus obtained powder was used as a reductively alkylated NCE5.

This powder was dissolved in 0.1 M ammonium bicarbonate buffer (pH 8.0). The solution was mixed with about 1/50 mole amount of trypsin (mfd. by Promega) based on the protein and subjected to the reaction at 37° C. overnight. By subjecting the digestion product to a column chromatography (column: C18 220×2.1 mm, 0.1% TFA in 5% acetonitrile to 0.085% TFA in 35% acetonitrile gradient) using Model 172μ Preparative HPLC System (mfd. by PE Applied Biosystems), 5 peptides were separated. Amino acid sequence of each of the thus obtained peptide fragments was determined by a protein sequencer Model 492 (mfd. by PE Applied Biosystems). The results are as follows.

```
                                           (SEQ ID NO:4)
T-28.8:
Leu-Lys-Pro-Gly-Cys-Tyr-Trp-Arg
                  (8 residues)

(SEQ ID NO:5)
T-32.6:
Tyr-Trp-Asp-Cys-Cys-Lys
                  (6 residues)

(SEQ ID NO:6)
T-35.9:
Trp-Asp-Asn-Pro-Leu-Phe-Asp-Gly-Gly-Asn-Thr-Arg
                  (12 residues)

(SEQ ID NO:7)
T-39.8:
Gln-Trp-Cys-Cys-Ala-Cys-Tyr-Glu-Leu-Thr-Phe-Thr
                  (12 residues)

(SEQ ID NO:8)
T-43.0:
Phe-Asp-Trp-Phe-Leu-Asn-Ala-Asp-Asn-Pro-Ser-Val-
Asn-Trp-Arg
     * * * * * *   (15 residues)
```

Among the N-terminal amino acid sequence and the amino acid sequences obtained by peptide mapping, 4 peptides were identical to the *Humicola grisea* eg14 sequence reported by S. Takashima et al. (S. Takashima et al., *Journal of Biotechnology*, 67, 85–97 (1999)). However, the same sequence was not found in T-43.0. Accordingly, it was suggested that, though the sequence shows homology, it is not the same but a novel protein.

Example 3

Cloning of Cellulase NCE5 cDNA (1) Isolation of cDNA and Preparation of Library

For the screening of the gene of a cellulase component NCE5, mRNA was prepared from *Humicola insolens* MN200-1 and a library was prepared by synthesizing cDNA using a reverse transcriptase.

(i) Preparation of Total RNA

*Humicola insolens* MN200-1 was cultured in a cellulase inducing medium, preferably the (N) medium described in Example 1, for 2 days and the resulting cells were recovered by centrifugation (3,500 rpm, 10 minutes). A 3 g portion of the cells were washed with sterile water, frozen with liquid nitrogen and then pulverized using a mortar and a pestle in liquid nitrogen. Total RNA was isolated from the thus pulverized cells using ISOGEN (mfd. by Nippon Gene) in accordance with the manual attached thereto, and the total RNA was confirmed as a stained image by a formaldehyde agarose gel electrophoresis.

(ii) Preparation of Poly(A) Tail+RNA (=mRNA)

A 1 mg portion of the total RNA prepared in the step (i) was applied to an oligo(dT) cellulose column using mRNA Purification Kit (mfd. by Amersham Pharmacia Biotech) in accordance with the manual attached thereto, and mRNA was eluted and isolated. The mRNA was then confirmed as a smear stained image by a formaldehyde agarose gel electrophoresis.

(iii) Synthesis of cDNA

Using Time Saver cDNA Synthesis Kit (mfd. by Amersham Pharmacia Biotech) and in accordance with the manual attached thereto, cDNA was synthesized from 5 µg of the mRNA prepared in the step (ii).

(iv) Preparation of cDNA Library

An EcoRI-NotI adapter contained in the above Time Saver cDNA Synthesis Kit was connected to blunt ends of the thus synthesized total cDNA in accordance with the manual attached thereto. Entire portion of the DNA fragments were connected to the EcoRI arm of a phage vector λ ZAP II Cloning Kit (mfd. by Stratagene) using DNA Ligation Kit Ver. 2 (mfd. by Takara Shuzo), subjected to ethanol precipitation and then dissolved in TE (10 mM Tris-HCl pH 8.0, 1 mM EDTA) buffer. The thus obtained recombinant phage vector was subjected to in vitro packaging using Gigapack III Plus Packaging Extract (mfd. by Stratagene) in accordance with the manual attached thereto. Thereafter, *Escherichia coli* XL1-Blue MRF' was infected with the recombinant phage and cultured on a plate medium, and the thus formed plaques were used as a phage library. Using this library, the gene of interest was cloned.

(2) Amplification of DNA by PCR and Its Analysis

Using the cDNA prepared in the step (1)-(iii) as the template and based on the information of the partial amino acid sequence of Example 2, DNA was amplified by PCR.

As the primers, the following synthetic oligonucleotides corresponding to the N-terminal and a part of the amino acid sequence of peptide T-43.0 shown by * were prepared.

```
                                              (SEQ ID NO:9)
N-         5'-TAY TGG GAY TGY TGY AAR CC-3' (20 mer)
terminal:

(SEQ ID NO:10)
T-43.0:    5'-TCI GCR TTI ARR AAC CAR TC-3' (20 mer)
```

The PCR was carried out using 1 µg of cDNA as the template under the following conditions in 50 µl of a reaction solution containing 1.25 units of LA Taq DNA polymerase (mfd. by Takara Shuzo) and the buffer solution attached thereto, 0.2 mM dNTP, 10% DMSO and 1 µM of each primer. At 94° C. for 1 minute, (94.0° C., 30 seconds, 55.0° C., 30 seconds, 72.0° C., 1 minute)×25 times and then at 72.0° C. for 5 minutes.

A DNA fragment of about 500 bp was amplified by this reaction, and its sequencing was carried out using DYEnamic ET terminator cycle sequencing premix Kit (mfd. by Amersham Pharmacia Biotech) and ABI PRISM 310 Genetic Analyzer (mfd. by PE Applied Biosystems) in accordance with the attached protocol. As a result, the amino acid sequence deduced from the thus determined nucleotide sequence contained all of the partial amino acid sequence obtained in Example 2. Accordingly, this was used as a probe in the following screening.

(3) Cloning of Cellulase Component NCE5 Gene (i) Screening by Plaque Hybridization A 100 ng portion of the 500 bp DNA fragment amplified by PCR was labeled in advance using ECL Direct DNA/RNA Labeling Detecting System (mfd. by Amersham Pharmacia Biotech).

The phage plaques prepared in (1)-(iv) were transferred on Hybond-N+Nylon Transfer Membrane (mfd. by Amersham Pharmacia Biotech), alkali-treated with 0.4N sodium hydroxide to denature the recombinant phage DNA on the membrane into single-stranded one, washed with 5×SSC (1×SSC: 15 mM trisodium citrate, 150 mM sodium chloride) and then air-dried to fix the DNA. Thereafter, the hybridization and detection reaction were carried out in accordance with the manual of the kit and then sensitization was effected on FUJI MEDICAL X-RAY FILM (mfd. by Fuji Photo Film) to obtain 6 positive clones.

(ii) Preparation of Phage DNA

DNA was prepared as plasmid DNA from the positive clones in accordance with the manual attached to the kit.

A plasmid in which the DNA fragment was cloned into pBluescript SK(-) was prepared from an ampicillin resistant *E. coli* strain SOLR™, and PCR was carried out under the same conditions described in the foregoing, using this as the template and using the N-terminal and T-43.0 primers used in the step (2). As a result, a 500 bp amplified product was obtained from one plasmid. Thus, since it was presumed that the DNA of interest was cloned into this plasmid, this was digested with EcoRI and subjected to an agarose gel electrophoresis.

As a result, it contained an EcoRI fragment of about 1 kbp.

(4) Determination of cDNA Nucleotide Sequence

Nucleotide sequence of the EcoRI fragment of about 1 kbp inserted into the positive recombinant pBluescript SK(-) plasmid, obtained in the step (3)-(ii), was determined by the same method using T3 and T7primers. As a result, this nucleotide sequence contained a 672 bp ORF, with the nucleotide sequence and an amino acid sequence deduced from the ORF respectively shown in SEQ ID NO:2 and SEQ ID NO:1 of SEQUENCE LISTING.

Also, since the sequence after the 18th position amino acid counting from the N-terminal of this deduced protein coincided with the N-terminal sequence of 25 kDa protein determined in the step (1) of Example 2, it was revealed that this gene encodes the 25 kDa protein.

In addition, it was considered that the sequence of from the 1st to 18th amino acids of this ORF is a signal sequence for secreting the protein into the extracellular moiety.

Example 4

Expression of NCE5 Gene in *Humicola insolens*

An expression vector for use in *Humicola insolens* MN200-1 was constructed in the following manner making use of a plasmid pJD01 obtained in accordance with the method described in International Publication WO 00/24879.

(1) Construction of NCE5 Expression Plasmid pJND-c5

(i) Introduction of Site-directed Mutation into NCE5 Gene

The NCE5 gene was amplified by PCR by designing primers in such a manner that the sequence just upstream of the initiation codon and just downstream of the termination codon contained BamHI in advance, so that they can be connected to the BamHI site of the plasmid pJD01. The primers for mutagenesis use were designed as follows.

```
                                           (SEQ ID NO:11)
NCE5-N-BamHI
5'-GGGGATCCTGGGACAAGATGCAGCTCCCCCTGACCACG-3'
                                           (38 mer)

(SEQ ID NO:12)
NCE5-C-BamHI
5'-GGGGATCCTGCATTTAACGCGAGCAGCCGCTCTTGGCC-3'
                                           (38 mer)
```

The PCR reaction was carried out under the same conditions using the positive recombinant pBluescript SK(−) plasmid obtained in Example 3 as the template. As a result, an amplified product of a DNA fragment of about 670 bp was confirmed by a 1.0% agarose gel electrophoresis. Thus, unreacted substances were removed by Micro Spin S-400 HR Columns (mfd. by Amersham Pharmacia Biotech), and the product was subjected to ethanol precipitation and digested with BamHI. Next, its entire portion was subjected to 1.0% agarose gel electrophoresis, the 670 bp DNA fragment was recovered using Sephaglas BandPrep Kit (mfd. by Amersham Pharmacia Biotech) in accordance with the attached manual and its BamHI fragment was subcloned into the BamHI site of a plasmid pUC118, thereby obtaining a plasmid pNCE5Bam shown in FIG. 1. Nucleotide sequence of the inserted fragment was then determined and confirmed by the method described in the foregoing.

(ii) Preparation of Plasmid pJND-c5

Figure 2:
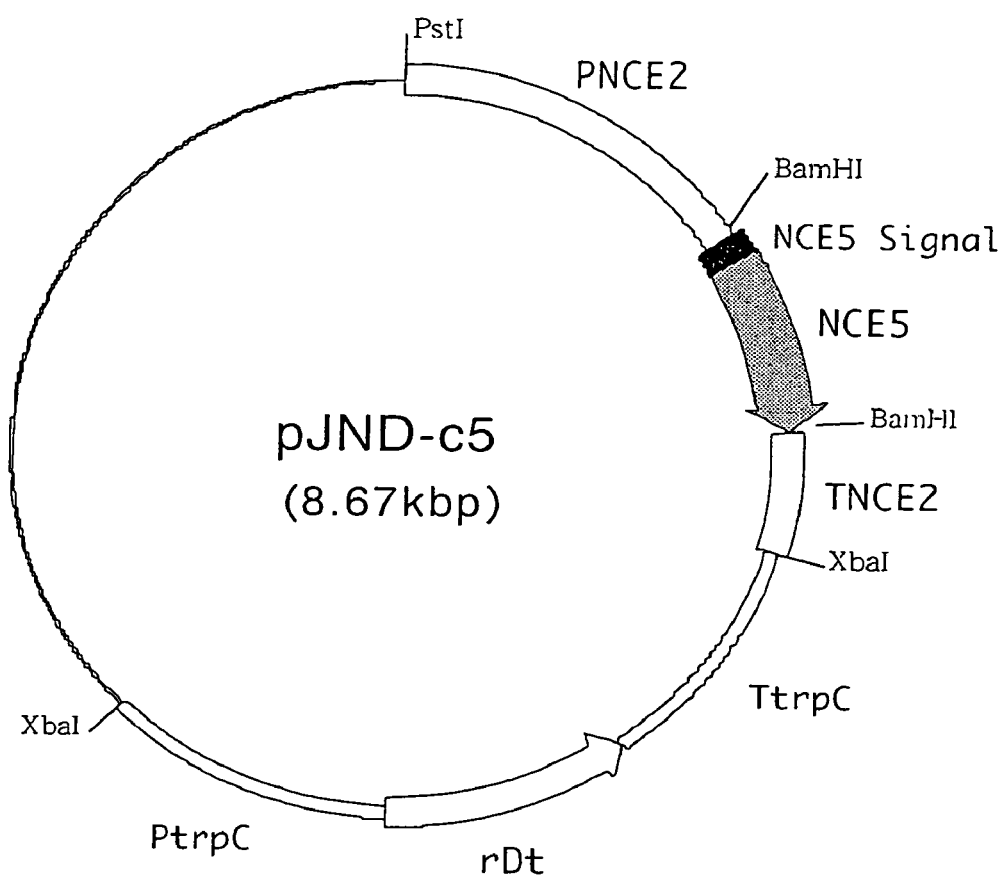
FIG. 2 represents a constitution of plasmid pJND-c5.

The plasmid pJD01 described in International Publication WO 00/24879 was digested with BamHI and separated by a 0.8% agarose gel electrophoresis, and a DNA fragment of about 8.0 Kbp was recovered using the Sephaglas BandPrep Kit and subjected to dephosphorylation using an E. coli alkalinephosphatase (mfd. by Takara Shuzo) in accordance with the attached manual. Also, the plasmid pNCE5Bam obtained in the above step (i) was digested with BamHI in the same manner, and a 670 bp DNA fragment was recovered and connected using DNA Ligation Kit Ver. 2 to obtain an expression plasmid pJND-c5 shown in FIG. 2.

(2) Transformation of *Humicola insolens* with Plasmid pJND-c5

*Humicola insolens* MN200-1 was cultured in an (S) medium at 37° C. for 24 hours and then the cells were collected by 10 minutes of centrifugation at 3,000 rpm. The (S) medium has a composition in which glucose (3.0%) is added to the (N) medium described in Example 1 and Avicel is removed therefrom. The thus obtained cells were washed with 0.5 M sucrose and suspended in 10 ml of a protoplast forming enzyme solution (3 mg/ml β-glucuronidase, 1 mg/ml chitinase, 1 mg/ml zymolyase, 0.5 M sucrose) which had been filtered through a 0.45 µm filter. By shaking this at 30° C. for 60 to 90 minutes, the hyphae were made into protoplasts. This suspension was filtered and then centrifuged at 2,500 rpm for 10 minutes to recover the protoplasts which were then washed with SUTC buffer (0.5 M sucrose, 10 mM calcium chloride, 10 mM Tris-HCl (pH 7.5)).

The thus prepared protoplasts were suspended in 1 ml of SUTC buffer, and a 100 µl portion of the suspension was mixed with 10 µg of DNA (TE) solution (10 µl) and allowed to stand in ice for 5 minutes. Next, this was mixed with 400 µl of a PEG solution (60% PEG 4000, 10 mM calcium chloride, 10 mM Tris-HCl (pH 7.5)), and the mixture was allowed to stand in ice for 20 minutes, mixed with 10 ml of SUTC buffer and then. centrifuged at 2,500 rpm for 10 minutes. The thus collected protoplasts were suspended in 1 ml of SUTC buffer, centrifuged at 4,000 rpm for 5 minutes and then finally suspended in 100 µl of SUTC buffer.

The thus treated protoplasts were overlaid on a hygromycin (200 µg/ml)-containing YMG medium (1% glucose, 0.4% yeast extract, 0.2% malt extract, 1% agar (pH 6.8))) together with YMG soft agar and cultured at 37° C. for 5 days, and the thus formed colonies were used as transformants.

Example 5

Culturing and Identification of pJND-c5 Transformants (1) Evaluation by SDS-PAGE The plasmid pJND-c5 was introduced into *Humicola insolens* MN200-1 as described above, and 40 strains showing hygromycin resistance were selected. They were cultured at 37° C. for 5 days in the (N) medium, and the thus obtained culture supernatants were analyzed by 12%-SDS-PAGE mini (mfd. by Tefco) electrophoresis to find that a 25 kDa protein considered to be NCE5 was particularly increased in 12 clones.

(2) Identification of N-Terminal Amino Acid Residues of Recombinant NCE5

In order to confirm that the protein expressed in a large amount in the above step (1) is originated from the NCE5 gene, its N-terminal amino acid sequence was determined. Firstly, the culture supernatant was separated by the 12%-SDS-PAGE mini electrophoresis, the resulting proteins were electrically transferred on a PVDF membrane in accordance with the method of Example 2, and the protein having a molecular weight of 25 kDa was treated to remove its modified N-terminal residue and then subjected to a protein sequencer. As a result, it coincided with the cellulase NCE5 N-terminal amino acid sequence deduced from the nucleotide sequence of the plasmid pJND-c5.

Example 6

Evaluation of the Activity of NCE5 Expressed in *Humicola insolens* to Abrade Dyed-denim Cellulose-containing Fabric Using the culture broth of NCE5 gene-expressed *Humicola insolens* obtained in Example 5 and a culture broth of *Humicola insolens*, abrasive treatment of a pair of desized 12 ounce blue jeans pants was carried out under the following conditions. The culture broth of NCE4 gene-expressed *Humicola insolens* was obtained by shaking culture of a transformant obtained by introducing an expression plasmid pEGD01 into *Humicola insolens* MN200-1 in accordance with the description of International Publication WO 98/03640. The transformant was cultured by shaking at 37° C. for 5 days in (N) culture. The culture broth of *Humicola insolens* was obtained by shaking culture of *Humicola insolens* MN200-1 at 37° C. for 5 days.

| | |
|---|---|
| Testing machine (mfd. by Sanyo Electric, full automatic washer SCW 5101) | 20 kg washer |
| Temperature | 65° C. |
| Time | 60 minutes |
| pH | 6.2 (6.7 mM phosphate buffer) |

To the treating solution were added an appropriate amount of rubber balls together with each cellulase preparation solution.

As the abrasion degree, a Lab display system L value (lightness) was measured using a spectrophotometer (mfd. by Minolta, CM-525i). By calculating increased L value (increased lightness) based on the control (untreated fabric), namely ΔL value, the degree of abrasion was evaluated by this ΔL value. That is, 10 points of ΔL value (n=10) were measured for each test denim and their average value was calculated. Based on this, concentration of endoglucanase as protein necessary for obtaining a ΔL value of about 6 was calculated.

The protein concentration was determined by preparing a standard curve with bovine serum albumin using Protein Assay Kit (mfd. by Bio-Rad Laboratories).

The results are as shown in Table 1.

TABLE 1

| Sample | Protein concentration |
| --- | --- |
| Humicola insolens culture broth | 80.0 mg/liter |
| NCE4-expressed H. insolens culture broth | 6.0 mg/liter |
| NCE5-expressed H. insolens culture broth | 6.0 mg/liter |

Example 7

Evaluation of Back-staining in the Abrasion of Dyed-denim Cellulose-containing Fabric by NCE5 Expressed in Humicola insolens Using the culture broths of NCE5 gene-expressed Humicola insolens and NCE4 gene-expressed Humicola insolens obtained in Example 5, abrasion of dyed-denim cellulose-containing fabric was carried out at various temperatures. Concentration of the enzyme to be added was defined as an amount necessary for obtaining a ΔL value of about 6 at 65° C.

For the evaluation of back-staining, whiteness of a sheet of white cotton cloth sewed on the dyed-denim cellulose-containing texture was measured after the test as a Lab display system L value (lightness) using a spectrophotometer (mfd. by Minolta, CM-525i). The larger L value means whiter white cloth and lower degree of back-staining.

The results are as shown in Table 2. In comparison with NCE4, NCE5 showed larger degree of abrasion and lower degree of back-staining at each reaction temperature, so that lower degree of back-staining by NCE5 is evident from this result.

TABLE 2

| Enzyme | Reaction temperature | Abrasion degree (ΔL) | Back-staining degree (L) |
| --- | --- | --- | --- |
| NCE5 | 65° C. | 6.00 | 74.99 |
|  | 55° C. | 8.32 | 75.10 |
|  | 45° C. | 7.74 | 75.33 |
| NCE4 | 65° C. | 5.88 | 74.53 |
|  | 55° C. | 7.29 | 74.17 |
|  | 45° C. | 6.30 | 74.56 |

Example 8

Evaluation of the Action of NCE5 Expressed in Humicola insolens to Remove Fuzz from a Regenerated Cellulose Fabric by a Launder Meter The activity of NCE5 expressed in Humicola insolens, obtained in Example 5, to remove fuzz from a typical example of regenerated cellulose fabric, lyocell, was evaluated in the following manner.

A fuzz was raised on a previously dyed sheet of lyocell knit cloth (mfd. by Toyoshima, Japan) in a large washer together with a surfactant and rubber balls. Thereafter, the thus fuzz-raised lyocell knit cloth (mfd. by Toyoshima, Japan, 10 cm×10 cm) was subjected to a lyocell fuzz removal treatment under the following conditions to calculate the protein concentration of NCE5 expressed in Humicola insolens required for removing the formed fuzz completely.

| Testing machine (Daiei Kagaku Seiki MFG., Japan) | Launder Meter L-12 |
| --- | --- |
| Temperature | 55° C. |
| Time | 60 minutes |
| Reaction solution | 40 ml |
| Reaction pH | pH 5 (10 mM acetate buffer) |

To the treating solution were added appropriate amount of rubber balls together with the endoglucanase solution.

It was revealed as the result that the fuzz is completely removed by adding the enzyme in a protein concentration of 6 mg/L.

Example 9

Evaluation of the Action of NCE5 Expressed in Humicola insolens to Remove Fuzz from Cotton when Formulated as a Detergent The activity of NCE5 expressed in Humicola insolens, obtained in Example 5, to remove fuzz from cotton was evaluated in the following manner. That is, a fuzz was raised on a sheet of cotton knit cloth (2 cm×15 cm) in a large washer using the culture supernatant of NCE5 expressed in Humicola insolens, prepared in Example 5, together with a surfactant and rubber balls, and the resulting cloth was subjected to a fuzz removal treatment under the following conditions. The protein concentration required for completely removing the formed fuzz was calculated.

| Testing machine (Daiei Kagaku Seiki MFG., Japan) | Launder Meter L-12 |
| --- | --- |
| Temperature | 40° C. |
| Time | 120 minutes |
| Reaction solution | 40 ml |
| Reaction pH | pH 9.3 |

(5 mM sodium carbonate-sodium bicarbonate buffer)
(Nonionic Surfactant)
Persoft NK-100 (mfd. by Nippon Oil & Fats) 0.20 g/L
(Anionic Surfactant)
LAS (mfd. by Wako Pure Chemical Industries) 0.10 g/L To the treating solution were added appropriate amount of rubber balls together with the endoglucanase solution.

As a result, the fuzz was completely removed with a protein concentration of 45 mg/L and color clarification of cloth became possible.

In addition, bending resistance of cotton knit was measured in accordance with the 45° cantilever method of JIS L1096. As a result, the migration length of a cotton knit test piece treated without adding the enzyme was 127 mm, but the migration length of a cotton knit test piece treated by adding 15 mg/L (protein concentration) of NCE5 was 81 mm which evidently showed its softening.

Example 10

Evaluation of the Effect of NCE5 Expressed in *Humicola insolens* to Improve Freeness of Paper Pulp A culture broth of NCE5-expressed *Humicola insolens* was added as a protein quantity of 60 µg to 6 g dry weight of unbleached kraft pulp derived from a broad-leaved tree and subjected to 1 hour of the reaction at 50° C. in 270 ml of 50 mM citrate buffer (pH 6.0). The enzyme was inactivated by boiling the mixture for 10 minutes, and then the freeness (CSF) was measured in accordance with JIS P-8121.

The results are shown in Table 3.

TABLE 3

| Sample | CSF (ml) |
| --- | --- |
| Enzyme non-addition plot | 492 |
| NCE5-expressed *Humicola insolens* culture broth | 519 |

All publications, patents and patent applications cited herein are incorporated in the present specification by reference in their entirety.

INDUSTRIAL APPLICABILITY

The endoglucanase enzyme NCE5 of the invention can be used in detergent compositions and is also useful in deinking waste paper, improving freeness of paper pulp and improving properties of cellulose-containing fabrics, such as removal of fuzz, improvement of the touch and appearance, color clarification, localized variation in color and reduction of stiffness.

---

The invention claimed is:

1. An isolated protein having endoglucanase activity, which comprises positions 19 to 223 of SEQ ID NO:1.

2. The protein of claim 1, further comprising positions 1 to 18 of SEQ ID NO:1 in the N-terminal side.

3. The protein according to claim 1, wherein it is isolated from a mold.

4. The protein according to claim 3, wherein the mold belongs to the genus *Humicola*.

5. The protein according to claim 4, wherein the mold belongs to *Humicola insolens*.

6. An isolated polynucleotide component which comprises a polynucleotide sequence coding for the protein of claim 1.

7. An isolated polynucleotide component which comprises the polynucleotide sequence described in SEQ ID NO:2.

8. An expression vector which comprises the polynucleotide sequence described in claim 6.

9. An isolated host cell transformed with the expression vector described in claim 8.

10. The host cell according to claim 9, wherein it is a yeast or a mold.

11. The host cell according to claim 10, wherein the yeast belongs to the genus *Saccharomyces*, the genus *Hansenula* or the genus *Pichia*.

12. The host cell according to claim 11, wherein the yeast is *Saccharomyces cerevisiae*.

13. The host cell according to claim 10, wherein the mold belongs to the genus *Humicola*, the genus *Aspergillus*, the genus *Trichoderma*, the genus *Fusarium* or the genus *Acremonium*.

14. The host cell according to claim 10, wherein the mold is *Humicola insolens, Aspergillus niger* or *Aspergillus oryzae, Trichoderma viride, Fusarium oxysporum* or *Acremonium cellulolyticus*.

15. A method for producing an isolated protein having endoglucanase activity, which comprises positions 19 to 223 of SEQ ID NO:1, which comprises the steps of culturing the host cell of claim 9 and subsequently collecting the protein from the host cell and/or its culture mixture.

16. An isolated protein having endoglucanase activity, which comprises positions 19 to 223 of SEQ ID NO:1 produced by culturing a host cell transformed with the expression vector of claim 8 and collecting the protein from the host cell and/or its culture mixture.

17. A cellulase preparation which comprises the protein of claim 1.

18. A method for treating a cellulose-containing fabric, which comprises a step of allowing the cellulose-containing fabric to contact with the protein of claim 1.

19. A method of reducing the rate at which a cellulose-containing fabric becomes fuzzy or of reducing fuzzing in a cellulose-containing fabric, which comprises a step of allowing the cellulose-containing fabric to contact with the protein of claim 1.

20. A method of weight loss treatment for a cellulose-containing fabric to improve its touch and appearance, which comprises a step of allowing the cellulose-containing fabric to contact with the protein of claim 1.

21. A method of providing color clarification of colored cellulose-containing fabric, which comprises a step of treating the colored cellulose-containing fabric with the protein of claim 1.

22. A method for providing a localized variation in color of a colored cellulose-containing fabric, which comprises a step of treating the colored cellulose-containing fabric with the protein of claim 1.

23. A method of reducing the rate at which a cellulose-containing fabric becomes stiff or of reducing stiffness in a cellulose-containing fabric, which comprises a step of treating the cellulose-containing fabric with the protein of claim 1.

24. The method according to claim 18, wherein the treatment of fabric is carried out through soaking, washing and rinsing of the fabric.

25. A detergent additive agent which comprises the protein of claim 1 in a non-scattering granular form or a stabilized liquid form.

26. A detergent composition which comprises the protein of claim 1.

27. A method for deinking waste paper, which comprises treating the waste paper with the protein of claim 1 and a deinking agent.

28. A method for improving freeness of paper pulp, which comprises a step of treating paper pulp with the protein of claim 1.

29. A method for improving digestion ability of animal feed, which comprises a step of treating a cellulose-containing fiber with the protein of claim 1.

* * * * *